(12) United States Patent
Kase et al.

(10) Patent No.: US 8,323,934 B2
(45) Date of Patent: Dec. 4, 2012

(54) PROCESS FOR PRODUCING FATTY ACIDS

(75) Inventors: Minoru Kase, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 1176 days.

(21) Appl. No.: 12/067,245

(22) PCT Filed: Oct. 6, 2006

(86) PCT No.: PCT/JP2006/320425
§ 371 (c)(1),
(2), (4) Date: Mar. 18, 2008

(87) PCT Pub. No.: WO2007/043631
PCT Pub. Date: Apr. 19, 2007

(65) Prior Publication Data
US 2010/0184168 A1    Jul. 22, 2010

(30) Foreign Application Priority Data

Oct. 6, 2005  (JP) .................. 2005-293277
Oct. 6, 2005  (JP) .................. 2005-293278

(51) Int. Cl.
*C12N 11/00* (2006.01)
*C12N 11/14* (2006.01)
*C12N 11/16* (2006.01)
*C12P 1/00* (2006.01)
*C12P 7/00* (2006.01)
*C12P 7/40* (2006.01)
*C12P 7/64* (2006.01)

(52) U.S. Cl. .......... 435/134; 435/41; 435/132; 435/136; 435/174; 435/176

(58) Field of Classification Search ........................ None
See application file for complete search history.

(56) References Cited

FOREIGN PATENT DOCUMENTS

| EP | 1 008 647 | 6/2000 |
|---|---|---|
| WO | 94 23051 | 10/1994 |
| WO | WO 2004/111164 A1 | 12/2004 |

OTHER PUBLICATIONS

Elvig et al: "Combined Enzymatic/Non-Enzymatic Fat Splitting", Research Disclosure, XP000305037, No. 336, pp. 310, 1992.
Office Action issued Oct. 13, 2010, in China Patent Application No. 200680036703.3 (with English translation).

*Primary Examiner* — Debbie K Ware
(74) *Attorney, Agent, or Firm* — Oblon, Spivak, McClelland, Maier & Neustadt, L.L.P.

(57) ABSTRACT

A process for producing fatty acid by hydrolyzing oil and fat, which comprises: a first step of partially hydrolyzing oil and fat by either of the following method (a) or (b), and a second step of hydrolysis by the other method: (a) enzymatic hydrolysis using an immobilized enzyme which is an enzyme immobilized on a support and (b) high pressure and temperature hydrolysis. A method of efficiently producing fatty acid with a reduced content of trans-unsaturated fatty acid in the constituent fatty acids and having a good appearance with reduced coloring by hydrolysis of oil and fat is provided.

19 Claims, No Drawings

PROCESS FOR PRODUCING FATTY ACIDS

FIELD OF THE INVENTION

The present invention relates to a process for producing fatty acids by hydrolyzing oil and fat.

BACKGROUND OF THE INVENTION

Production of fatty acids is carried out by hydrolyzing oil and fat. High pressure and temperature hydrolysis (JP-A-2003-113395) or enzymatic hydrolysis (JP-A-2000-160188) is employed as a method of hydrolyzing oil and fat. The former method is performed under high temperature and pressure conditions in the presence of water and has an advantage of high productivity. However, when a raw material containing a large amount of unsaturated fatty acid is used in this method, a large amount of trans-unsaturated fatty acid is produced depending on the conditions in some cases. On the other hand, the latter method is performed under reaction conditions having a low temperature of 0 to 70° C. in the presence of an enzyme such as lipase as a catalyst, and as a result, this method has low productivity compared to the high pressure and temperature hydrolysis method although no trans-unsaturated fatty acid is produced.

Further, high pressure and temperature hydrolysis has an induction period at an initial stage of the reaction before decomposition starts. To avoid or shorten the induction time, there is a technique in which glyceride is first partially hydrolyzed by enzymatic hydrolysis using the 1,3-position specific lipase to prepare partially hydrolyzed glyceride, and then high pressure and temperature hydrolysis is performed (JP-A-8-507917).

DISCLOSURE OF THE INVENTION

The present invention relates to a process for producing fatty acids by hydrolyzing oil and fat, which includes a first step of partially hydrolyzing oil and fat by either of the following method (a) or (b), and a second step of hydrolysis by the other method:

(a) enzymatic hydrolysis using an immobilized enzyme which is an enzyme immobilized on a support and (b) high pressure and temperature hydrolysis.

DETAILED DESCRIPTION OF THE INVENTION

Recently, there is a growing interest in the impact of edible oil on health. Scientific research has proved that trans-unsaturated fatty acid as well as saturated fatty acid and cholesterol increase LDL (low-density lipoprotein) cholesterol levels and increase the risk of coronary heart disease. Thus, reduction of the content of trans-unsaturated fatty acid in edible oil is desired.

Unrefined raw material oil and fat for which a deodorizing step is omitted contains 1.5% by weight or less of trans-unsaturated fatty acid in the constituent fatty acids. When the raw material oil and fat are hydrolyzed by enzymatic hydrolysis, the content of the trans-unsaturated fatty acid in the constituent fatty acids does not increase. In this case, however, since the color of the raw material remains unchanged, the resulting fatty acid has a poor appearance. On the other hand, fatty acid obtained by hydrolyzing unrefined raw material oil and fat only by high pressure and temperature hydrolysis has a good appearance because coloring components are decomposed, but the content of trans-unsaturated fatty acid in the constituent fatty acids is high.

It has been found that the method described in JP-A-8-507917 can shorten the reaction time of hydrolysis of oil and fat by high pressure and temperature hydrolysis and thus fatty acid can be efficiently produced, and as a consequence, fatty acid with a reduced content of trans-unsaturated fatty acid in the constituent fatty acids can be produced. However, it has been proven that when hydrolysis is performed by high pressure and temperature hydrolysis after partial hydrolysis by enzymatic hydrolysis, fatty acid with a good color tone cannot necessarily be produced. Then it has been found that the cause is the form of the enzyme used.

Accordingly, the present invention provides a process for producing fatty acids by hydrolysis of oil and fat capable of efficiently producing fatty acid with a reduced content of trans-unsaturated fatty acid in the constituent fatty acids and having a good appearance with reduced coloring.

Under such circumstances, the present inventors have conducted studies on the combination of enzymatic hydrolysis and high pressure and temperature hydrolysis in a hydrolysis reaction of oil and fat, and have found that when (a) oil and fat are first partially hydrolyzed by enzymatic hydrolysis using an immobilized enzyme which is an enzyme immobilized on a support (first step) and then (b) hydrolyzed by high pressure and temperature hydrolysis (second step), fatty acid with a reduced content of trans-unsaturated fatty acid in the constituent fatty acids and good appearance can be efficiently produced.

The present inventors have also found that when (b) oil and fat are first partially hydrolyzed by high pressure and temperature hydrolysis (first step) and then (a) hydrolyzed by enzymatic hydrolysis using an immobilized enzyme which is an enzyme immobilized on a support (second step) as well, fatty acid with a reduced content of trans-unsaturated fatty acid in the constituent fatty acids and monoacylglycerol and good appearance can be produced. It has also been found that when the process is performed in the opposite order, the content of trans-unsaturated fatty acid in the constituent fatty acids is decreased but the content of monoacylglycerol is not decreased.

According to the present invention, fatty acid with a reduced content of trans-unsaturated fatty acid in the constituent fatty acids and good appearance can be efficiently produced by hydrolysis of oil and fat.

"(a) Enzymatic hydrolysis using an immobilized enzyme which is an enzyme immobilized on a support" (hereinafter simply "enzymatic hydrolysis") in the present invention refers to a method of preparing fatty acid and glycerol, including adding water to raw material oil and fat and allowing the mixture to react using an immobilized enzyme which is an enzyme immobilized on a support, such as lipase, as a catalyst at a low temperature condition. "(b) High pressure and temperature hydrolysis" in the present invention refers to a method of preparing fatty acid and glycerol, including adding water to raw material oil and fat and allowing the mixture to react in a high temperature and pressure condition. The "fatty acid" in the present invention includes not only fatty acids but also those in which glycerol, monoacylglycerol, diacylglycerol and/or triacylglycerol are present.

In the present invention, the raw material oil and fat to be hydrolyzed may be vegetable oil and fat and animal oil and fat. Specific examples of raw materials include rapeseed oil, sunflower oil, corn oil, soybean oil, linseed oil, rice bran oil, safflower oil, cottonseed oil, beef tallow and fish oil. In addition, those obtained by fractionating or mixing the above oil and fat and those in which the composition of fatty acid is adjusted by hydrogenation or transesterification can be used as the raw material. However, oil and fat without hydrogenation are preferred for reducing the content of trans-unsaturated fatty acid in the constituent fatty acids of the raw material oil and fat.

In an aspect of the present invention, it is preferred that after obtaining oil and fat from plants or animals which are each raw materials, solid matters other than oil are removed by filtration, centrifugation or the like. Then, water, or in some cases acid, is further added to the raw material oil and fat and mixed, and preferably degumming is performed by separating gum components by centrifugation or the like. Further, after adding alkali and mixing, preferably the raw material oil and fat is deacidified by washing with water and dehydrating. Further, the raw material oil and fat is preferably decolorized by bringing into contact with an adsorbent such as activated clay and separating the adsorbent by filtration or the like. Preferably, these treatments are performed in the above order, but the order may be changed. In addition to these, in order to remove wax, the raw material oil and fat may be subjected to wintering, which is a step of separating solid matters at low temperatures. The raw material oil and fat may also be deodorized by bringing into contact with steam under reduced pressure according to need. Upon this, keeping thermal history as low as possible is preferred so as to reduce the content of trans-unsaturated fatty acid in the constituent fatty acids of oil and fat. For the condition of the deodorization step, the temperature is controlled to preferably 300° C. or lower, more preferably 270° C. or lower, and the time is preferably 10 hours or less, more preferably 5 hours or less.

In the present invention, raw material oil and fat with a content of trans-unsaturated fatty acid in the constituent fatty acids of preferably 1.5% by weight or less, more preferably 1% by weight or less, even more preferably 0.5% by weight or less are used for reducing the content of trans-unsaturated fatty acid in the constituent fatty acids of fatty acid after hydrolysis. For example, undeodorized oil and fat is preferably used as a part or all of the raw material oil and fat, because trans-unsaturated fatty acid in the constituent fatty acids can be reduced. Herein, when two or more oils and fats are used, the content of trans-unsaturated fatty acid in the constituent fatty acids means the total amount of trans-unsaturated fatty acid in the two or more oils and fats.

In high pressure and temperature hydrolysis, the higher the degree of unsaturation of constituent fatty acids of raw material oil and fat, the more easily trans-unsaturated fatty acid is formed by heating. Specifically, while trans-unsaturated fatty acid is hardly formed by heating in the case of oleic acid having a degree of unsaturation of 1, the formation of trans-unsaturated fatty acid is remarkable in the case of a fatty acid having a degree of unsaturation of 2 or more, such as linoleic acid and linolenic acid.

The content of trans-unsaturated fatty acid in the constituent fatty acids of the raw material oil and fat used in the process of the present invention is preferably 1.5% by weight or less, more preferably 0.01 to 1% by weight, even more preferably 0.1 to 1% by weight in terms of physiological effects. The raw material oil and fat has a color tone C of preferably 20 or more, more preferably 35 or more because the effect of improving the appearance according to the present invention is significantly exhibited.

The "content of trans-unsaturated fatty acid in constituent fatty acids" and the "composition of fatty acid" in the present invention means values obtained by measuring a sample, which is fatty acid methyl ester prepared in accordance with "Preparation of Fatty Acid Methyl Esters (2.4.1.2-1996)" in "Standard Methods for the Analysis of Fats, Oils and Related Materials" edited by Japan Oil Chemists' Society, by American Oil Chemists' Society Official Method Ce 1f-96 (GLC method). The "color tone C" of raw material oil and fat or fatty acid is measured by American Oil Chemists' Society Official Method Ca 13e-92 (Lovibond method) with a 5.25 inch cell and calculated by the following formula (1).

$$\text{Color tone } C = 10R + Y \quad (1)$$

(in the formula, R=Red value, Y=Yellow value)

In the present invention, in enzymatic hydrolysis of oil and fat, an immobilized enzyme which is an enzyme immobilized on a support needs to be used. In an aspect of the present invention, lipase is preferred as an enzyme for decomposing oil and fat used in enzymatic hydrolysis. Not only lipase derived from animals or plants, but also commercially available lipase derived from microorganisms may be used. Examples of enzymes for decomposing oil and fat include lipase derived from microorganisms such as *Rhizopus* species, *Aspergillus* species, *Chromobacterium* species, *Mucor* species, *Pseudomonas* species, *Geotrichum* species, *Penicillium* species and *Candida* species and animal lipase such as pancreatic lipase. To achieve a high hydrolysis rate, lipase having no site specificity (random type) is preferred, and lipase derived from microorganisms such as the *Pseudomonas* species and *Candida* species is preferred.

Examples of immobilization supports include inorganic supports such as celite, diatomaceous earth, kaolinite, silica gel, molecular sieves, porous glass, activated carbon, calcium carbonate and ceramics, ceramics powder, and organic polymers such as polyvinyl alcohol, polypropylene, chitosan, ion exchange resin, hydrophobic adsorbent resin, chelating resin and synthetic adsorbent resin. In view of water holding ability, ion exchange resin is preferred. Of the ion exchange resins, porous ion exchange resins are preferred because they can adsorb a large amount of lipase as they have a large surface area.

The resin used as an immobilization support has a particle size of preferably 100 to 1000 µm, more preferably 250 to 750 µm. Preferably, the resin has a pore diameter of 10 to 150 nm. Examples of such resin materials include phenol formaldehyde, polystyrene, acrylamide and divinyl benzene resins, and among them, phenol formaldehyde resins (e.g., Duolite A-568 available from Rohm and Hass) are preferred.

When immobilizing an enzyme, the enzyme may be directly adsorbed to a support, but to create an adsorption condition which produces high activity, supports may be used after treating with a fat-soluble fatty acid or a derivative thereof before adsorbing the enzyme. Examples of a fat-soluble fatty acid to be used include saturated or unsaturated, linear or branched fatty acid having 8 to 18 carbon atoms whose hydroxyl group may be substituted. Specific examples thereof include capric acid, lauric acid, myristic acid, oleic acid, linoleic acid, α-linolenic acid, recinoleic acid and isostearic acid. Examples of derivatives thereof include esters of these fatty acids and mono- or polyhydric alcohol, phospholipids and derivatives obtained by adding ethylene oxide to these esters. Specific examples thereof include methyl ester and ethyl ester of the above-described fatty acid, monoglyceride, diglyceride, ethylene oxide adducts thereof, polyglycerol ester, sorbitan ester and sucrose ester thereof. These fat-soluble fatty acid or derivatives thereof may be used in combination of two or more.

For bringing these fat-soluble fatty acids or derivatives thereof into contact with a support, these fat-soluble fatty acids or derivatives thereof may be directly added to a support in water or an organic solvent. To improve dispersibility, however, fat-soluble fatty acid or derivatives thereof may be once dispersed or dissolved in an organic solvent and then added to a support dispersed in water. Examples of organic solvents include chloroform, hexane and ethanol. The fat-soluble fatty acid or derivatives thereof is used in an amount of preferably 1 to 500 parts by weight, more preferably 10 to 200 parts by weight based on 100 parts by weight of the support. The temperature upon contact is preferably 0 to 100° C., more preferably 20 to 60° C. The time for contact is about 5 minutes to 5 hours. The support after completion of the treatment is collected by filtration, and it may be dried. The drying temperature is room temperature to 100° C. Drying may be performed under reduced pressure.

The temperature at which an enzyme is immobilized on a support can be determined according to characteristics of the enzyme. Temperatures at which enzymes are not deactivated, specifically, 0 to 60° C. are preferred, and 5 to 40° C. are more preferred. The pH range of the enzyme solution used for immobilization may be such that the enzyme is not denatured, and can be determined according to characteristics of the enzyme as is the temperature. Preferably, the pH is 3 to 9. A buffer is used for maintaining the pH, and examples of such buffers include acetate buffers, phosphate buffers and tris-HCL buffers. Preferably, in terms of efficiency of immobilization, the enzyme solution has a sufficient concentration of the enzyme which is not more than the saturation solubility of the enzyme. Supernatant obtained by removing insoluble portions by centrifugation according to need or a solution purified by ultrafiltration or the like can also be used as an enzyme solution. While the weight of the enzyme used varies depending on the activity of the enzyme, the weight is preferably 5 to 1000 parts by weight, more preferably 10 to 500 parts by weight based on 100 parts by weight of the support.

To make conditions suitable for the hydrolysis reaction after immobilization of the enzyme, preferably the immobilized enzyme is collected from the enzyme solution by filtration and unnecessary water is removed, and then without drying, the immobilized enzyme is brought into contact with oil and fat such as soybean oil which is a reaction substrate. The moisture content in the immobilized enzyme after contact varies depending on the type of the support to be used, and is preferably 0.1 to 100 parts by weight, more preferably 1 to 50 parts by weight, even more preferably 5 to 50 parts by weight based on 100 parts by weight of the immobilization support. Here, the immobilized enzyme is put in a container such as a column, and oil and fat may be circulated through the column with a pump, or the immobilized enzyme may be dispersed in oil and fat. The temperature upon contact is preferably 20° C. to 60° C., and can be selected according to characteristics of the enzyme. The time for contact is about 1 to 48 hours. In view of industrial productivity, the immobilized enzyme is preferably collected by filtration upon completion of the contact.

The hydrolysis activity range of the immobilized enzyme is preferably 20 U/g or more, more preferably 100 to 10000 U/g, even more preferably 500 to 5000 U/g. Here, 1 U of the enzyme means hydrolyzability of an enzyme producing 1 μmol of free fatty acid per minute when hydrolysis is performed by mixing a mixture of oil and fat:water=100:25 (weight ratio) while stirring at 40° C. for 30 minutes.

In the present invention, partial hydrolysis of oil and fat by enzymatic hydrolysis or high pressure and temperature hydrolysis performed in the first step and hydrolysis of oil and fat by high pressure and temperature hydrolysis or enzymatic hydrolysis performed in the second step may be performed batch-wise, continuously or semi-continuously. The immobilized enzyme packed in a tower may be used or the immobilized enzyme may be used in an agitation tank, but to prevent collapse of the immobilized enzyme, the immobilized enzyme packed in a tower is preferably used. Partially hydrolyzed fatty acid and water may be fed to a reactor concurrently or countercurrently. Preferably, the raw material oil and fat and water fed to a hydrolysis reactor are previously degassed or deoxidized in order to prevent oxidation of fatty acid.

The amount of the immobilized enzyme used for enzymatic hydrolysis reaction may be accordingly determined based on the activity of the enzyme. The immobilized enzyme is used in an amount of preferably 0.01 to 30 parts by weight, more preferably 0.1 to 20 parts by weight, particularly preferably 1 to 10 parts by weight based on 100 parts by weight of the raw material oil and fat to be decomposed. Further, water is used in an amount of preferably 10 to 200 parts by weight, more preferably 20 to 100 parts by weight, even more preferably 30 to 80 parts by weight based on 100 parts by weight of fatty acid to be decomposed. This water may be distilled water, ion exchange water, degassed Water, tap water or well water. Such water may contain other water-soluble components such as glycerol. Where necessary, a buffer of pH 3 to 9 may be used so as to maintain the stability of the enzyme.

The reaction temperature is adjusted to preferably 0 to 70° C., more preferably 20 to 50° C. at which the activity of the enzyme is effectively brought out and free fatty acid produced by decomposition is not crystallized. Preferably, the reaction is performed in the presence of inert gas so as to avoid contact with air as much as possible.

The hydrolysis reaction of oil and fat by enzymatic hydrolysis or high pressure and temperature hydrolysis may be controlled based on the fatty acid concentration and terminated when a predetermined fatty acid concentration is reached. The "fatty acid concentration" in the present invention refers to a value obtained by measuring the acid value and the composition of fatty acid and calculating by the following formula (2) according to "Yushi Seihin no Chishiki (Oil and Fat Products)" (Saiwaishobo Ltd.). The acid value is measured by the American Oil Chemists' Society Official Method Ca 5a-40.

$$\text{Fatty acid concentration (\% by weight)} = x \times y/56.1/10 \qquad (2)$$

(x=acid value [mgKOH/g], y=average molecular weight determined from the composition of fatty acid)

Preferred examples of reactors used for high pressure and temperature hydrolysis include a countercurrent Colgate-Emery process oil and fat decomposition tower equipped with a hydrolysis reaction vessel having a capacity of 7 to 40 m³ (made by, for example, IHI). For decomposition on a small scale, commercially available laboratory scale autoclave systems (made by, for example, Nitto Kouatsu Co., Ltd.) may be used as the hydrolysis reaction vessel.

Of the processes of the present invention, a process including a first step of partial hydrolysis by (a) enzymatic hydrolysis is described.

Oil and fat are partially hydrolyzed by enzymatic hydrolysis until the fatty acid has a concentration of preferably 20 to 90% by weight, more preferably 25 to 85% by weight, even more preferably 30 to 80% by weight in terms of industrial productivity, good appearance and prevention of the generation of trans-unsaturated fatty acid. After the partial hydrolysis, the content of trans-unsaturated fatty acid in the constituent fatty acids is preferably 0 to 1.5% by weight, more preferably 0 to 1% by weight, even more preferably 0 to 0.7% by weight. Preferably, the amount of the total nitrogen in the partially hydrolyzed fatty acid used for high pressure and temperature hydrolysis is small in order to make the color tone of the fatty acid hydrolyzed by high pressure and temperature hydrolysis better. The amount of the total nitrogen is preferably 2 ppm or less, more preferably 1.5 ppm or less, even more preferably 0.1 to 1.5 ppm. In the same point of view, the increase in the amount of the total nitrogen of the oil which has been hydrolyzed by an enzyme from the amount of the total nitrogen in the raw material to be hydrolyzed by the enzyme is preferably 50% by weight or less, more preferably 20% by weight or less, even more preferably 0 to 15% by weight.

In the process of the present invention, when oil and fat are partially hydrolyzed by enzymatic hydrolysis in the first step, it is then necessary to perform hydrolysis by high pressure and temperature hydrolysis (second step). In the present invention, the high pressure and temperature hydrolysis is performed under the following reaction conditions.

In the high pressure and temperature hydrolysis which is the second step, preferably 10 to 250 parts by weight of water is added to 100 parts by weight of partially hydrolyzed fatty acid, thereby performing hydrolysis under conditions of a temperature of 200 to 270° C. and a pressure of 2 to 8 MPa for 0.1 to 6 hours. In terms of industrial productivity and decoloration of fatty acid and prevention of the generation of trans-unsaturated fatty acid, the temperature is preferably 210 to 265° C., more preferably 215 to 260° C. In the same point of view, the amount of water added to 100 parts by weight of partially hydrolyzed fatty acid is more preferably 15 to 150 parts by weight, even more preferably 20 to 120 parts by weight. In the same point of view, the pressure is more preferably 2 to 7 MPa, even more preferably 2.5 to 6 MPa. In the same point of view, the reaction time is more preferably 0.2 to 5 hours, even more preferably 0.3 to 4 hours.

The partially hydrolyzed fatty acid used for high pressure and temperature hydrolysis of oil and fat, which is the second step, may be directly used, but the fatty acid and the aqueous phase may be separated by a method such as standing separation or centrifugation according to need. Further, purification may be performed by removing glycerol distributed in the oil phase by centrifugation or water washing according to need.

The hydrolysis reaction of oil and fat by high pressure and temperature hydrolysis, which is the second step, may be controlled based on the fatty acid concentration shown by the aforementioned formula (2) and terminated when a predetermined fatty acid concentration is reached. After completion of the hydrolysis reaction, preferably the fatty acid and the aqueous phase are separated by a method such as standing separation or centrifugation. Purification may be performed by removing glycerol distributed in the oil phase by centrifugation, water washing or the like according to need.

In the process of the present invention, in the hydrolysis reaction of oil and fat, 0.01 to 30 parts by weight of an immobilized enzyme and 10 to 200 parts by weight of water are each added to 100 parts by weight of raw material oil and fat to perform partial hydrolysis by enzymatic hydrolysis at 0 to 70° C. (first step), and then 10 to 250 parts by weight of water is added to 100 parts by weight of partially hydrolyzed fatty acid to perform hydrolysis under conditions of a temperature of 200 to 270° C. and a pressure of 2 to 8 MPa for 0.1 to 6 hours in the second step as described above. Accordingly, fatty acid having a good appearance with a reduced content of trans-unsaturated fatty acid in the constituent fatty acids can be obtained with increased industrial productivity.

Of the processes of the present invention, a process including a first step of partial hydrolysis by (b) high pressure and temperature hydrolysis is now described.

In the high pressure and temperature hydrolysis which is the first step, preferably 10 to 250 parts by weight of water is added to 100 parts by weight of oil and fat, thereby performing hydrolysis under conditions of a temperature of 200 to 270° C. and a pressure of 2 to 8 MPa for 0.1 to 6 hours. In terms of industrial productivity and decoloration of fatty acid and prevention of the generation of trans-unsaturated fatty acid, the temperature is preferably 210 to 265° C., more preferably 215 to 260° C. In the same point of view, the amount of water added to 100 parts by weight of oil and fat is more preferably 15 to 150 parts by weight, even more preferably 20 to 120 parts by weight. In the same point of view, the pressure is more preferably 2 to 7 MPa, even more preferably 2.5 to 6 MPa. In the same point of view, the reaction time is more preferably 0.2 to 5 hours, even more preferably 0.3 to 4 hours.

The hydrolysis reaction of oil and fat under high temperature and pressure conditions may be controlled based on fatty acid concentration and terminated when a predetermined fatty acid concentration is reached. Herein, the "fatty acid concentration" is determined by the aforementioned formula (2).

Oil and fat is partially hydrolyzed by high pressure and temperature hydrolysis in the first step until the fatty acid has a concentration of preferably 0.5 to 90% by weight, more preferably 1.5 to 85% by weight, even more preferably 20 to 70% by weight in terms of industrial productivity, good appearance and prevention of generation of trans-unsaturated fatty acid and monoglyceride. After the partial hydrolysis, the partially hydrolyzed fatty acid has a color tone C of preferably 35 or less, more preferably 1 to 30, even more preferably 5 to 25 and the content of trans-unsaturated fatty acid in the constituent fatty acids is preferably 0 to 1.5% by weight, more preferably 0.1 to 1.2% by weight, even more preferably 0.2 to 0.7% by weight. Further, the content of monoglyceride is preferably 1 to 20% by weight, more preferably 1 to 15% by weight, even more preferably 3 to 10% by weight.

In the process of the present invention, when oil and fat are partially hydrolyzed by high pressure and temperature hydrolysis in the first step, it is then necessary to perform hydrolysis by enzymatic hydrolysis in the second step.

In an aspect of the present invention, when hydrolysis of oil and fat is performed by enzymatic hydrolysis in the second step, preferably an immobilized enzyme which is an enzyme immobilized on a support is used for effective utilization of the activity of the enzyme, although enzyme powder may also be used. Lipase supported on an immobilization support is preferably used as the immobilized enzyme.

In the present invention, hydrolysis of oil and fat by enzymatic hydrolysis in the second step is performed under the following reaction conditions.

The amount of immobilized enzyme used for enzymatic hydrolysis reaction may be accordingly determined based on the activity of the enzyme. The immobilized enzyme is used in an amount of preferably 0.01 to 30 parts by weight, more preferably 0.1 to 15 parts by weight, even more preferably 0.2 to 10 parts by weight based on 100 parts by weight of the fatty acid to be decomposed. Further, water is used in an amount of preferably 10 to 200 parts by weight, more preferably 20 to 100 parts by weight, even more preferably 30 to 80 parts by weight based on 100 parts by weight of the fatty acid to be decomposed. This water may be distilled water, ion exchange water, tap water or well water. Such water may contain other water-soluble components such as glycerol. Where necessary, a buffer of pH 3 to 9 may be used so as to maintain the stability of the enzyme.

The partially hydrolyzed fatty acid used for enzyme hydrolysis reaction of oil and fat, which is the second step, may be directly used, but the fatty acid and the aqueous phase may be separated by a method such as standing separation or centrifugation according to need. Further, purification may be performed by removing glycerol distributed in the oil phase by centrifugation, water washing or the like.

The hydrolysis reaction of oil and fat by enzyme hydrolysis, which is the second step, may be controlled based on the fatty acid concentration shown by the aforementioned formula (2) and terminated when a predetermined fatty acid concentration is reached. After completion of the hydrolysis reaction, preferably the fatty acid and the aqueous phase are separated by a method such as standing separation or centrifugation. Further, purification may be performed by removing glycerol distributed in the oil phase by centrifugation, water washing or the like.

In the process of the present invention, in the hydrolysis reaction of oil and fat, 10 to 250 parts by mass of water is added to 100 parts by weight of oil and fat to perform partial hydrolysis under conditions of a temperature of 200 to 270° C. and a pressure of 2 to 8 MPa for 0.1 to 6 hours (first step), and then 0.01 to 30 parts by weight of an immobilized enzyme and 10 to 200 parts by weight of water are each added to 100 parts by weight of the partially hydrolyzed fatty acid to perform hydrolysis at 0 to 70° C. as described above. Accordingly, fatty acid having a good appearance with reduced contents of trans-unsaturated fatty acid and monoacylglycerol can be obtained with increased industrial productivity.

EXAMPLES

A. Study of a Process Having Method (a) in the First Step and Method (b) in the Second Step

[Method of Producing an Immobilized Enzyme]

50 g of Duolite A-568 (available from Rohm & Hass) was stirred in 500 mL of a 0.1 N aqueous sodium hydroxide solution for an hour. Subsequently, washing was performed with 500 mL of distilled water for an hour and the pH was kept constant with 500 mL of a 500 mM phosphate buffer (pH7) for 2 hours. Thereafter, the pH was kept constant with 500 mL of a 50 mM phosphate buffer (pH7) twice every 2 hours. Subsequently, the support was collected by filtration and replacement with ethanol was performed with 250 mL of ethanol for 30 minutes. After filtration, 250 mL of ethanol containing 50 g of recinoleic acid was added thereto and recinoleic acid was adsorbed to the support for 30 minutes. Thereafter, the support was collected by filtration and washed with 250 mL of a 50 mM phosphate buffer (pH7) 4 times to remove ethanol, and the support was collected by filtration. Then, the support was brought into contact with 1000 mL of a 10% solution of commercially available lipase (lipase AY "Amano" 30G available from Amano Enzyme Inc.) which acts on oil and fat for 4 hours to immobilize the enzyme on the support. Filtration was then performed to collect the immobilized enzyme and washing was performed with 250 mL of a 50 mM acetate buffer (pH7) to remove enzyme or protein which was not immobilized. These procedures were all performed at 20° C. The immobilization rate was determined from the difference between the remaining activity of the enzyme solution after immobilization and the activity of the enzyme solution before immobilization to be 95%. Subsequently, 200 g of deodorized soybean oil was added thereto, the mixture was stirred at 40° C. for 2 hours, and the deodorized soybean oil was separated by filtration to provide an immobilized enzyme. The immobilized enzyme thus obtained was washed with undeodorized soybean oil which was the substrate actually used for reaction three times and filtrated before use.

[Raw Material Oil and Fat]

The undeodorized soybean oil shown in Table 1 was used as raw material oil and fat. The glyceride composition was measured by the method shown in the following.

[Method of Measuring Glyceride Composition]

10 mg of a sample and 0.5 mL of a trimethylsilylating agent ("Silylating agent TH" available from Kanto Chemical Co., Inc.) were put in a sample bottle. The bottle was sealed and heated at 70° C. for 15 minutes. Thereto were added 1.0 mL of distilled water and 2.0 mL of hexane, and after mixing, the hexane layer was analyzed by gas chromatography (GLC).

Apparatus: Model 6890 made by Hewlett Packard
Column: DB-1HT (available from J&W Scientific) 7 m
Column temperature: initial=80° C., final=340° C.
Temperature increase rate: 10° C./minute, kept at 340° C. for 20 minutes
Detector: FID, temperature=350° C.
Injection part: split ratio=50:1, temperature=320° C.
Sample injection amount: 1 μL
Carrier gas: helium, flow rate=1.0 ml/minute

[Measurement of Amount of Total Nitrogen]

5 g of undeodorized soybean oil and partially hydrolyzed fatty acid were weighed in a 10 mL volumetric flask and the amount of the total nitrogen of a sample adjusted with toluene was measured by a total trace nitrogen analyzer. Pyridine/toluene solutions of various concentrations were used as the standard solution.

Apparatus: Total trace nitrogen analyzer made by Mitsubishi Chemical Corporation Model TN-05
Temperature: INLET 800° C./CATALYST 900° C.
Used gas and flow rate: oxygen 600 mL/min helium/oxygen Sub 100/100 mL/min
Time: helium 30 seconds/oxygen 120 seconds
Sample injection amount and injection rate: 50 μL, 1.0 μL/second

TABLE 1

|  | Fatty acid concentration [% by weight] | Color tone C 10R + Y | Total nitrogen [ppm] | Trans-unsaturated fatty acid [% by weight] | Glycerol [% by weight] | MAG [% by weight] | DAG [% by weight] | TAG [% by weight] |
|---|---|---|---|---|---|---|---|---|
| Undeodorized soybean oil | 0.1 | 52 | 1.2 | 0.0 | 0.0 | 0.0 | 1.7 | 98.3 |
| Sample A | 36.2 | 57 | 1.2 | 0.0 | 0.0 | 2.3 | 18.3 | 43.2 |
| Sample B | 61.3 | 56 | 1.2 | 0.0 | 0.0 | 2.6 | 16.5 | 19.6 |
| Sample C | 35.4 | 59 | 1.5 | 0.0 | 0.0 | 2.5 | 20.1 | 42.0 |
| Sample D | 38.5 | 61 | 2.1 | 0.0 | 0.0 | 2.9 | 25.4 | 33.2 |

MAG: monoacylglycerol
DAG: diacylglycerol
TAG: triacylglycerol

[Enzymatic Hydrolysis Using Immobilized Enzyme]

The undeodorized soybean oil shown in Table 1 was hydrolyzed by enzymatic hydrolysis using an immobilized enzyme. The hydrolysis reaction was performed by circulating a reaction solution through an enzyme column packed with the immobilized enzyme and a substrate circulating vessel.

20.0 g on a dry basis of the immobilized enzyme (hydrolysis activity 2960 U/g) washed with undeodorized soybean oil was packed into a stainless steel enzyme column (bore diameter 22 mm, height 145 mm) equipped with a jacket. The original weight of the immobilized enzyme on a dry basis was determined by removing oil attached to the immobilized enzyme of a batch packed in the stainless steel enzyme column equipped with a jacket using acetone and hexane and dehydrating under reduced pressure.

900 g of undeodorized soybean oil and 540 g of distilled water were put in a substrate circulating vessel of 3 L capacity with a bore diameter of 150 mm equipped with a jacket, and the mixture was mixed and heated to 40° C. while stirring (semicircular blade φ 90 mm×H 25 mm, 600 r/min). During this period, the gas phase in the substrate circulating vessel equipped with a jacket was replaced with nitrogen to form nitrogen atmosphere.

After heating the substrate to 40° C., the substrate in the substrate circulating vessel equipped with a jacket was supplied to the stainless steel enzyme column equipped with a jacket from the top at a flow rate of 55 mL/min using a liquid supply pump. The reaction solution from the bottom of the stainless steel enzyme column equipped with a jacket was returned to the substrate circulating vessel equipped with a jacket to start batchwise circulation reaction. 1 hour after the start of the reaction, the whole reaction solution was drawn to a 3 L beaker from the substrate circulating vessel equipped with a jacket. The aqueous phase was removed by allowing to stand at 40° C. for 120 minutes under nitrogen atmosphere to provide sample A. Part of sample A was sampled and centrifuged (5,000×g, 10 minutes) to remove the aqueous phase. The resulting partially hydrolyzed fatty acid was then completely dehydrated at 70° C. for 10 minutes under a vacuum of 400 Pa, and then analyzed.

Further, the stainless steel enzyme column equipped with a jacket packed with the immobilized enzyme used for preparing sample A was washed with undeodorized soybean oil. Then, batchwise circulation reaction was started under the same conditions as in the case of sample A. 3 hours after the start of the reaction, the whole reaction solution was drawn to a 3 L beaker from the substrate circulating vessel equipped with a jacket, and the aqueous phase was removed by allowing to stand at 40° C. for 120 minutes under nitrogen atmosphere to provide sample B. Sample B was analyzed after the same treatment as in the case of sample A. As a result of analysis of the resulting partially hydrolyzed fatty acid, the amount of the total nitrogen was the same as that in the undeodorized soybean oil and no detachment of enzyme occurred in the immobilized enzyme.

[Enzymatic Hydrolysis Using Lipase Powder]

The undeodorized soybean oil shown in Table 1 was hydrolyzed by enzymatic hydrolysis using lipase powder (lipase AY "Amano" 30 G available from Amano Enzyme Inc.). 1300 g of the undeodorized soybean oil and 750 g of distilled water were put in a four-neck flask of 3000 mL capacity. The mixture was mixed while stirring (semicircular blade φ 90 mm×H 25 mm, 300 r/min) and heated to 40° C. During this period, the gas phase in the four-neck flask of 3000 mL capacity was replaced with nitrogen to form nitrogen atmosphere. While stirring (semicircular blade φ 90 mm×H 25 mm, 300 r/min) at 40° C. under nitrogen atmosphere in a sealed state, thereto was added a whole mixture in which 3.9 g of lipase powder (lipase AY "Amano" 30G available from Amano Enzyme Inc.) was dissolved in 30 g of distilled water to start batchwise reaction while stirring. 0.6 hour after the start of the reaction, the whole reaction solution was drawn to a 3 L beaker from the four-neck flask of 3000 mL capacity. The aqueous phase was removed by allowing to stand at 40° C. for 120 minutes under nitrogen atmosphere to provide sample C. Sample C was analyzed after the same treatment as in the case of sample A.

[Enzymatic Hydrolysis Using Granulated Lipase]

The undeodorized soybean oil shown in Table 1 was hydrolyzed by enzymatic hydrolysis using granulated lipase (Lipolase 100T available from Novozymes A/S). 1300 g of the undeodorized soybean oil and 750 g of distilled water were put in a four-neck flask of 3000 mL capacity. The mixture was mixed while stirring (semicircular blade φ 90 mm×H 25 mm, 300 r/min) and heated to 45° C. During this period, the gas phase in the four-neck flask of 3000 mL capacity was replaced with nitrogen to form nitrogen atmosphere. While stirring (semicircular blade φ 90 mm×H 25 mm, 300 r/min) at 45° C. under nitrogen atmosphere in a sealed state, thereto was added a whole mixture in which 2.0 g of granulated lipase (Lipolase 100T available from Novozymes A/S) was dissolved in 30 g of distilled water to start batchwise reaction while stirring. 43 hours after the start of the reaction, the whole reaction solution was drawn to a 3 L beaker from the four-neck flask of 3000 mL capacity. The aqueous phase was removed by allowing to stand at 40° C. for 120 minutes under nitrogen atmosphere to provide sample D. Sample D was analyzed after the same treatment as in the case of sample A.

[High Pressure and Temperature Hydrolysis of Partially Hydrolyzed Fatty Acid and Undeodorized Soybean Oil]

High pressure and temperature hydrolysis was performed using samples A to D shown in Table 1 which are partially hydrolyzed fatty acids and undeodorized soybean oil as raw materials in a batch type autoclave system made by Nitto Kouatsu Co., Ltd. (capacity 2.2 L, design pressure 10 MPa, design temperature 300° C., material TB480H). 700 g of each of the raw materials and 350 g of distilled water were put in the autoclave system and the autoclave system was sealed. Then, an airtight test was performed using hydrogen at a pressure of 5.0 MPa to check that there is no leak in the autoclave system, and the air was replaced with nitrogen. Subsequently, while stirring at 600 r/min, the temperature was increased to 240° C. which was the reaction temperature. The time taken for temperature increase to 240° C. was 40 minutes and the ultimate pressure was 3.2 MPa. After reaching 240° C., the reaction solution was accordingly collected from a sampling port, sealed with nitrogen and rapidly cooled to 25° C. in a light shielding state. The reaction solution was then centrifuged (5,000 g, 5 minutes) to remove the aqueous phase, and the fatty acid phase was dehydrated at 70° C. for 5 minutes under a vacuum of 400 Pa. The acid value was measured and the fatty acid concentration was calculated. Hydrolysis was terminated when the fatty acid has a concentration of 85% by weight and the reaction solution was cooled to 50° C. The time taken for cooling to 50° C. was 50 minutes. The whole hydrolyzed fatty acid was drawn to a 2 L beaker from the autoclave system and the aqueous phase was removed by allowing to stand at 40° C. for 120 minutes under nitrogen atmosphere. Further, after removing the aqueous phase by centrifugation (5,000 g, 30 minutes), the resultant was put in a four-neck flask of 2000 mL capacity and the fatty acid was completely dehydrated at 70° C. for 30 minutes under a vacuum of 400 Pa while stirring (semicircular blade φ 90 mm×H 25 mm, 300 r/min) and analyzed. Fatty acid samples E to I shown in Table 2 were obtained.

TABLE 2

| | Reaction time [h] | Fatty acid concentration [% by weight] | Color tone C 10R + Y | Trans-unsaturated fatty acid [% by weight] | Glycerol [% by weight] | MAG [% by weight] | DAG [% by weight] | TAG [% by weight] |
|---|---|---|---|---|---|---|---|---|
| Sample E (raw material: undeodorized soybean oil) | 3.0 | 85.4 | 24 | 2.2 | 0.0 | 6.4 | 7.3 | 0.9 |
| Sample F (raw material: sample A) | 1.0 | 85.9 | 23 | 0.7 | 0.0 | 5.4 | 7.4 | 1.3 |
| Sample G (raw material: sample B) | 0.5 | 87.2 | 24 | 0.4 | 0.0 | 4.4 | 7.2 | 1.1 |
| Sample H (raw material: sample C) | 1.0 | 87.8 | 27 | 0.8 | 0.0 | 4.8 | 6.4 | 1.0 |
| Sample I (raw material: sample D) | 1.0 | 87.0 | 43 | 0.9 | 0.0 | 5.1 | 6.8 | 1.1 |

As is evident from Table 2, when raw material oil and fat are partially hydrolyzed by enzymatic hydrolysis using an immobilized enzyme so that fatty acid concentration is 20 to 90% by weight and then the resultant is hydrolyzed under high temperature and pressure conditions, fatty acids (samples F, G) not only with a low content of trans-unsaturated fatty acid in the constituent fatty acids but also having a good appearance can be prepared. On the contrary, it has been revealed that although the content of trans-unsaturated fatty acid in the constituent fatty acids is low in the fatty acids (samples H, I) obtained by partially hydrolyzing raw material oil and fat by enzymatic hydrolysis using lipase powder or granulated lipase and then hydrolyzing under high temperature and pressure conditions, the fatty acids have a poor appearance. It has also been revealed that although the fatty acid (sample E) obtained only by hydrolyzing raw material oil and fat under high temperature and pressure conditions has a good appearance, the content of trans-unsaturated fatty acid in the constituent fatty acids is high. Further, as is evident from Table 1 and Table 2, when fatty acid partially hydrolyzed by enzymatic hydrolysis has a small amount of total nitrogen, fatty acid hydrolyzed under high temperature and pressure conditions has a low color tone C.

B. Study of a Process Comprising Method (b) in the First Step and Method (a) in the Second Step

[Method of Producing Immobilized Enzyme]

50 g of Duolite A-568 (available from Rohm & Hass) was stirred in 500 mL of a 0.1 N aqueous sodium hydroxide solution for an hour. Subsequently, washing was performed with 500 mL of distilled water for an hour and the pH was kept constant with 500 mL of a 500 mM phosphate buffer (pH7) for 2 hours. Thereafter, the pH was kept constant with 500 mL of a 50 mM phosphate buffer (pH7) twice every 2 hours. Subsequently, the support was collected by filtration and replacement with ethanol was performed with 250 mL of ethanol for 30 minutes. After filtration, 250 mL of ethanol containing 50 g of recinoleic acid was added thereto and recinoleic acid was adsorbed to the support for 30 minutes. Thereafter, the support was collected by filtration and washed with 250 mL of a 50 mM phosphate buffer (pH7) 4 times to remove ethanol, and the support was collected by filtration. Then, the support was brought into contact with 1000 mL of a 10% solution of commercially available lipase (lipase AY "Amano" 30G available from Amano Enzyme Inc.) which acts on oil and fat for 4 hours to immobilize the enzyme on the support. Filtration was then performed to collect the immobilized enzyme and washing was performed with 250 mL of a 50 mM acetate buffer (pH7) to remove enzyme or protein which was not immobilized. These procedures were all performed at 20° C. The immobilization rate was determined from the difference between the remaining activity of the enzyme solution after immobilization and the activity of the enzyme solution before immobilization to be 95%. Subsequently, 200 g of soybean oil was added thereto, the mixture was stirred at 40° C. for 2 hours, and the soybean oil was separated by filtration to provide an immobilized enzyme. The immobilized enzyme thus obtained was washed with partially hydrolyzed fatty acid which was the substrate actually used for reaction and filtrated before use.

[Raw Material Oil and Fat]

The undeodorized soybean oil shown in Table 3 was used as raw material oil and fat, the glyceride composition was measured by the same method as described above.

TABLE 3

| Sample | Fatty acid concentration (% by weight) | Color tone C | Trans-unsaturated fatty acid (% by weight) | Glycerol (% by weight) | MAG (% by weight) | DAG (% by weight) | TAG (% by weight) |
|---|---|---|---|---|---|---|---|
| Undeodorized soybean oil | 0.1 | 41 | 0.0 | 0.0 | 0.0 | 1.1 | 98.9 |

MAG: monoacylglycerol
DAG: diacylglycerol
TAG: triacylglycerol

[High Pressure and Temperature Hydrolysis]

Raw material oil and fat were continuously supplied to an oil-water countercurrent high pressure hot water decomposition apparatus from the bottom and water was continuously supplied thereto from the top. The amounts supplied were such that 50 parts by weight of water was supplied based on 100 parts by weight of the raw material oil and fat. At this stage, the average residence time (hr) in the decomposition tower (volume of tower ($m^3$)/(flow rate of raw material oil and fat ($m^3$/hr)+flow rate of water ($m^3$/hr))) was about 4 hours.

The raw material oil and fat were heated by high pressure hot water (5.0 MPa, 240° C.) in the apparatus. The reaction solution was accordingly collected from a sampling port located along the oil-water countercurrent high pressure hot water decomposition apparatus, sealed with nitrogen and cooled to 25° C. in a light shielding state. The reaction solution was then centrifuged (5,000 g, 30 minutes) to remove the aqueous phase, and the fatty acid phase was dehydrated at 70° C. for 30 minutes under a vacuum of 400 Pa to provide samples J to N. The analysis values of each fatty acid are shown in Table 4.

TABLE 4

| Sample | Fatty acid concentration (% by weight) | Color tone C | Trans-unsaturated fatty acid (% by weight) | Glycerol (% by weight) | MAG (% by weight) | DAG (% by weight) | TAG (% by weight) |
| --- | --- | --- | --- | --- | --- | --- | --- |
| J | 90.6 | 19 | 1.9 | 0.0 | 4.2 | 5.2 | 0.0 |
| K | 78.6 | 20 | 1.0 | 0.1 | 7.1 | 11.7 | 2.6 |
| L | 47.2 | 21 | 0.4 | 0.4 | 7.3 | 21.7 | 23.3 |
| M | 1.7 | 27 | 0.0 | 0.0 | 0.1 | 2.2 | 95.9 |
| N | 92.0 | 18 | 2.0 | 0.0 | 3.1 | 4.9 | 0.0 |

[Hydrolysis By Enzymatic Hydrolysis (1)]

Samples J to M which are partially hydrolyzed fatty acids and the undeodorized soybean oil shown in Table 3 were hydrolyzed by enzymatic hydrolysis using an immobilized enzyme. 5 g (dry weight) of each immobilized enzyme (hydrolysis activity 2700 U/g) washed with samples J to M or the undeodorized soybean oil was weighed in a four-neck flask of 300 mL capacity. Thereto were added 100 g of corresponding samples J to M or the undeodorized soybean oil and 60 g of distilled water. While stirring (semicircular blade φ 60 mm×H 15 mm, 250 r/min) at 40° C. under nitrogen atmosphere in a sealed state, the reaction was continued until the fatty acids have a concentration of 93% by weight or higher. The reaction solution was centrifuged (5,000 g, 30 minutes) to remove the aqueous phase and the immobilized enzyme, and then the fatty acid phase was dehydrated at 70° C. for 30 minutes under a vacuum of 400 Pa to provide fatty acid (samples O to S). The analysis values of each fatty acid (in the case of using an immobilized enzyme) are shown in Table 5. For each sample, O was obtained by hydrolyzing J, P was obtained by hydrolyzing K, Q was obtained by hydrolyzing L, R was obtained by hydrolyzing M and S was obtained by hydrolyzing undeodorized soybean oil.

TABLE 5

| Sample | Reaction time (h) | Fatty acid concentration (% by weight) | Color tone C | Trans-unsaturated fatty acid (% by weight) | Glycerol (% by weight) | MAG (% by weight) | DAG (% by weight) | TAG (% by weight) |
| --- | --- | --- | --- | --- | --- | --- | --- | --- |
| O (raw material: J) | 0.5 | 93.8 | 20 | 1.9 | 0.0 | 0.4 | 3.9 | 1.9 |
| P (raw material: K) | 1.5 | 93.8 | 20 | 1.0 | 0.0 | 0.4 | 3.4 | 2.4 |
| Q (raw material: L) | 3.0 | 93.1 | 22 | 0.4 | 0.0 | 0.4 | 4.0 | 2.6 |
| R (raw material: M) | 6.0 | 93.2 | 28 | 0.0 | 0.0 | 0.5 | 4.2 | 2.1 |
| S (raw material: undeodorized soybean oil) | 6.0 | 93.0 | 48 | 0.0 | 0.0 | 0.5 | 5.3 | 1.2 |

[Hydrolysis By Enzymatic Hydrolysis (2)]

Samples J to M which are partially hydrolyzed fatty acids and the undeodorized soybean oil shown in Table 1 were hydrolyzed by enzymatic hydrolysis using enzyme powder. 100 g of samples J to M or the undeodorized soybean oil and 55 g of distilled water were weighed in a four-neck flask of 300 mL capacity. Thereto was added a whole mixture in which 0.1 g of lipase OF (derived from *Candida cylindracea* available from Meito Sangyo Co., Ltd.) was dissolved in 5 g of distilled water. While stirring (semicircular blade φ 60 mm×H 15 mm, 250 r/min) at 40° C. under nitrogen atmosphere in a sealed state, the reaction was continued until the fatty acids have a concentration of the fatty acid of 93% by weight or higher. The reaction solution was centrifuged (5,000 g, 30 minutes) to remove the aqueous phase and an intermediate layer in which lipase powder was present, and then the fatty acid phase was dehydrated at 70° C. for 30 minutes under a vacuum of 400 Pa to provide fatty acid (samples T to X). The analysis values of each fatty acid (in the case of using lipase powder) are shown in Table 6. For each sample, T was obtained by hydrolyzing J, U was obtained by hydrolyzing K, V was obtained by hydrolyzing L, W was obtained by hydrolyzing M and X was obtained by hydrolyzing undeodorized soybean oil.

TABLE 6

| Sample | Reaction time (h) | Fatty acid concentration (% by weight) | Color tone C | Trans-unsaturated fatty acid (% by weight) | Glycerol (% by weight) | MAG (% by weight) | DAG (% by weight) | TAG (% by weight) |
|---|---|---|---|---|---|---|---|---|
| T (raw material: J) | 0.2 | 94.0 | 22 | 1.9 | 0.0 | 0.5 | 3.0 | 2.5 |
| U (raw material: K) | 2.0 | 93.9 | 22 | 1.0 | 0.0 | 0.2 | 3.0 | 2.9 |
| V (raw material: L) | 6.0 | 93.7 | 23 | 0.4 | 0.0 | 0.4 | 3.2 | 2.7 |
| W (raw material: M) | 7.0 | 93.0 | 29 | 0.0 | 0.0 | 0.4 | 3.5 | 3.1 |
| X (raw material: undeodorized soybean oil) | 7.0 | 93.0 | 48 | 0.0 | 0.0 | 0.5 | 3.8 | 2.7 |

As is evident from Table 3 to Table 6, when raw material oil and fat are partially hydrolyzed under high temperature and pressure conditions so that the fatty acid concentration is 0.5 to 90% by weight and then the resultant is hydrolyzed by lipase, fatty acids (samples P, Q, R, U, V, W) not only with lower contents of trans-unsaturated fatty acid in the constituent fatty acids and monoacylglycerol but also having a good appearance can be prepared.

On the contrary, it has been revealed that although the fatty acid (sample N) obtained only by hydrolyzing raw material oil and fat under high temperature and pressure conditions has a good appearance, the contents of trans-unsaturated fatty acid in the constituent fatty acids and monoacylglycerol are high. It has also been revealed that although the fatty acids (samples O, T) obtained by partially hydrolyzing raw material oil and fat under high temperature and pressure conditions so that the fatty acid concentration is 90% by weight or higher and then hydrolyzing by lipase have a good appearance and the content of monoacylglycerol is low, the content of trans-unsaturated fatty acid in the constituent fatty acids is high.

Moreover, it has been revealed that although the contents of trans-unsaturated fatty acid in the constituent fatty acids and monoacylglycerol are low in the fatty acids (samples S, X) obtained only by enzyme hydrolysis reaction of raw material oil and fat, the fatty acids have a poor appearance.

The invention claimed is:

1. A process for producing fatty acids by hydrolyzing an oil or fat, which comprises:
    (i) first partially hydrolyzing the oil or fat by high pressure and temperature hydrolysis until the fatty acids in the oil or fat have a concentration of 1.5 to 85% by weight, and
    (ii) second hydrolyzing the product of (i) by enzymatic hydrolysis comprising contacting said oil or fat with an enzyme immobilized on a support.

2. The process for producing fatty acids according to claim 1, wherein said partially hydrolyzing the oil or fat by high pressure and temperature hydrolysis is performed until the fatty acids in the oil or fat have a concentration of 20 to 70% by weight.

3. The process for producing fatty acids according to claim 1, wherein the oil or fat subjected to partial hydrolysis contain 1.5% by weight or less of trans-unsaturated fatty acid in constituent fatty acids in the oil or fat.

4. The process for producing fatty acids according to claim 1, wherein said fatty acids comprises at least one fatty acid selected from the group consisting of glycerol, monoacylglycerol, diacylglycerol and triacylglycerol.

5. The process for producing fatty acids according to claim 1, wherein said oil or fat to be hydrolyzed is at least one selected from the group consisting of a vegetable oil, a vegetable fat, an animal oil, and an animal fat.

6. The process for producing fatty acids according to claim 1, wherein said oil or fat to be hydrolyzed is at least one selected from the group consisting of rapeseed oil, sunflower oil, corn oil, soybean oil, linseed oil, rice bran oil, safflower oil, cottonseed oil, beef tallow and fish oil.

7. The process for producing fatty acids according to claim 1, further comprising, prior to said hydrolyzing, removing solid matters other than oil by filtration or centrifugation.

8. The process for producing fatty acids according to claim 1, further comprising, prior to said hydrolyzing, at least one pre-processing step selected from the group consisting of degumming, deacidifying, decolorizing, wintering, and deodorizing.

9. The process for producing fatty acids according to claim 1, further comprising, prior to said hydrolyzing, deodorizing at a temperature of 300° C. for 10 hours or less.

10. The process for producing fatty acids according to claim 1, wherein said oil or fat to be hydrolyzed has a content of trans-unsaturated fatty acid in the constituent fatty acids of 1.5% by weight or less.

11. The process for producing fatty acids according to claim 1, wherein said oil or fat to be hydrolyzed has a color tone C of 20 or more.

12. The process for producing fatty acids according to claim 1, wherein the enzyme for enzymatic hydrolysis is a lipase.

13. The process for producing fatty acids according to claim 1, wherein said support is selected from the group consisting of celite, diatomaceous earth, kaolinite, silica gel, molecular sieves, porous glass, activated carbon, calcium carbonate, a ceramic, a ceramic powder, polyvinyl alcohol, polypropylene, chitosan, an ion exchange resin, a hydrophobic adsorbent resin, a chelating resin and a synthetic adsorbent resin.

14. The process for producing fatty acids according to claim 1, wherein said support is a resin and said resin has a particle size of 100 to 1000 μm.

15. The process for producing fatty acids according to claim 1, wherein said enzymatic hydrolysis is at a temperature of 20° C. to 60° C.

16. The process for producing fatty acids according to claim 1, wherein said high pressure and temperature hydrolysis comprises adding 10 to 250 parts by weight of water to 100 parts by weight of oil and fat and performing hydrolysis at a temperature of 200 to 270° C. and a pressure of 2 to 8 MPa for 0.1 to 6 hours.

17. The process for producing fatty acids according to claim 1, wherein following said high pressure and temperature hydrolysis, the resulting partially hydrolyzed fatty acid has a color tone C of 35 or less.

18. The process for producing fatty acids according to claim 1, wherein following said high pressure and temperature hydrolysis, the resulting partially hydrolyzed fatty acid has a content of trans-unsaturated fatty acid in the constituent fatty acids of 0 to 1.5% by weight.

19. The process for producing fatty acids according to claim 1, wherein following said high pressure and temperature hydrolysis, the resulting partially hydrolyzed fatty acid has a content of monoglyceride of 1 to 20% by weight.

* * * * *